(12) United States Patent
Muhanna et al.

(10) Patent No.: US 7,867,239 B2
(45) Date of Patent: Jan. 11, 2011

(54) VERTEBRAL PLATING SYSTEM

(75) Inventors: Nabil L. Muhanna, 2128 Vally Rd., Gainesville, GA (US) 30501; David L. Schalliol, Oakwood, GA (US)

(73) Assignee: Nabil L. Muhanna, Gainesville, GA (US)

( * ) Notice: Subject to any disclaimer, the term of this patent is extended or adjusted under 35 U.S.C. 154(b) by 415 days.

(21) Appl. No.: 11/431,131

(22) Filed: May 9, 2006

(65) Prior Publication Data
US 2007/0233110 A1  Oct. 4, 2007

Related U.S. Application Data

(60) Provisional application No. 60/782,162, filed on Mar. 14, 2006.

(51) Int. Cl.
*A61B 17/58* (2006.01)
(52) U.S. Cl. ........................................ 606/104; 606/305
(58) Field of Classification Search .................. 606/280, 606/300, 301, 305, 307, 308; 408/1 BD, 408/236, 239 A
See application file for complete search history.

(56) References Cited

U.S. PATENT DOCUMENTS

| 6,884,241 | B2 | 4/2005 | Bertranou et al. |
| 2003/0105462 | A1* | 6/2003 | Haider ........................ 606/69 |
| 2004/0260306 | A1* | 12/2004 | Fallin et al. .................. 606/104 |
| 2006/0008332 | A1* | 1/2006 | Greenberg et al. .......... 408/202 |

* cited by examiner

*Primary Examiner*—Eduardo C Robert
*Assistant Examiner*—Elana B Fisher
(74) *Attorney, Agent, or Firm*—Womble Carlyle Sandridge & Rice, PLLC

(57) ABSTRACT

A vertebral plating system includes a bone screw and a vertebral plate. The bone screw includes a screw head and a shaft. The screw head includes at least three segments flexibly attached to the shaft and has a spherical outside surface. The plate includes holes to receive the screw and that have a spherical inside surface. A driver tool has pins that are inserted into a pin hole on each segment, and that causes the segments to move towards each other when downward pressure is applied.

17 Claims, 5 Drawing Sheets

US 7,867,239 B2

VERTEBRAL PLATING SYSTEM

RELATED APPLICATIONS

This application claims the benefit of U.S. Provisional Patent Application No. 60/782,162 filed Mar. 14, 2006, the specification of which is herein incorporated by reference.

FIELD OF THE INVENTION

One embodiment of the present invention is directed to a medical device. More particularly, one embodiment of the present invention is a vertebral plating system that includes bone screws that are retained in a vertebral plate.

BACKGROUND INFORMATION

The human spine is a biomechanical structure consisting of thirty-three vertebral members and is responsible for protecting the spinal cord, nerve roots and internal organs of the thorax and abdomen. The spine also provides structural support for the body while permitting flexibility of motion.

Surgery on the spine may sometimes be necessary because of, for example, physical trauma or degenerative diseases. After spinal surgery, it is frequently necessary to apply a vertebral plate to lock adjacent vertebrae together to induce fusion of those vertebras. Medical bone screws are placed through the holes in the plates, and into the body of the vertebra. Often it is found that these screws do not find suitable core material in the bone to assure adequate long term mechanical strength, and the screws work loose and back out. The absence of a single screw over time in the assembly may not be detrimental to the success of fusion, but the screw becomes foreign matter in adjacent tissue and can cause severe complications to the patient.

There are numerous known plating systems that address this potential screw back-out problem, but they all require additional safety or backup hardware to retain the loose screws. Many require an internal set screw in the bone screw itself. This concept does what it is expected to do, but at the expense of the strength of the bone screw itself, as the screw has to be hollow. Other solutions require plates, tabs, or washers to retain the loose bone screw. In nearly every known solution, there is the potential of the solution becoming a problem. The more hardware installed, the more likely it is that there will be foreign matter getting into undesired places. There are the additional problems of complexity with all of these solutions. More things to tighten or secure means more work for the surgeon, and more levels of uncertainty.

Based on the foregoing, there is a need for an improved system and method for securing a vertebral plate to vertebrae with retaining screws.

SUMMARY OF THE INVENTION

One embodiment of the present invention is a vertebral plating system that includes a bone screw and a vertebral plate. The bone screw includes a screw head and a shaft. The screw head includes at least three segments flexibly attached to the shaft and has a generally spherical outside surface. The plate includes holes to receive the screw and that have a generally spherical inside surface. A driver tool has pins that are inserted into a pin hole on each segment, and that causes the segments to move towards each other when downward pressure is applied.

DETAILED DESCRIPTION

One embodiment of the present invention is a vertebral plate and bone screws that have spherical three segmented heads that enable the screws to be retained within the vertebral plate without requiring additional hardware. The specification and drawings of U.S. Provisional Patent Application No. 60/782,162, filed Mar. 14, 2006, are incorporated herein in their entirety by this reference.

Figure 1:
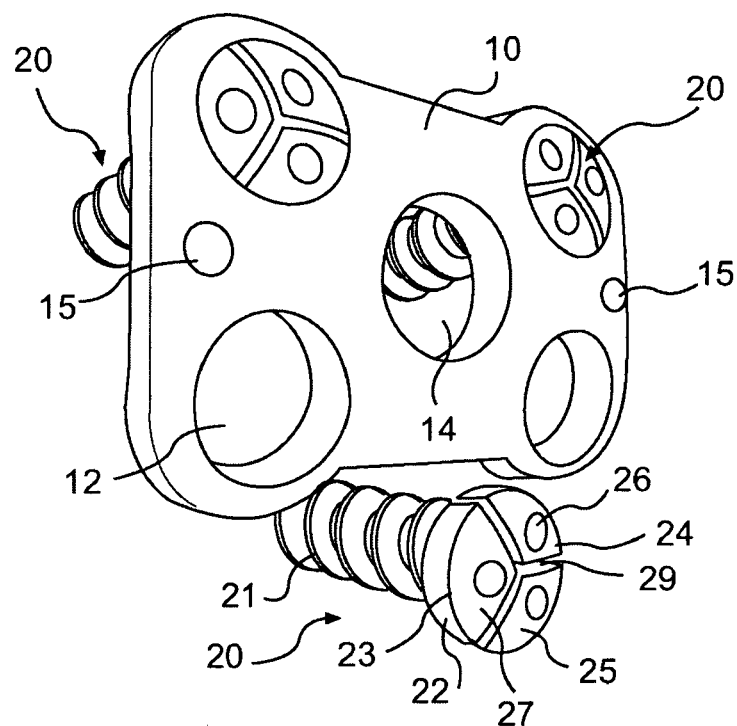
FIG. 1 is a perspective view of a vertebral plate and bone screws that are adapted to be inserted and retained by the vertebral plate in accordance with one embodiment of the present invention.

FIG. 1 is a perspective view of a vertebral plate 10 and bone screws 20 that are adapted to be inserted and retained by the vertebral plate in accordance with one embodiment of the present invention. Vertebral plate 10 includes screw holes 12 adapted to receive screws 20. Plate 10 further includes hole 14 which provides visibility to the surgeon when fastening plate 10 to vertebrae. Plate 10 further includes holes 15 which allow plate 10 to be temporarily pinned to vertebrae while screws 20 are fastened. Vertebral plate 10 is a single level plate, designed to connect two adjacent vertebrae. Other embodiments of vertebral plate 10 may be multiple level plates and would include additional holes 12 and screws 20. In one embodiment, plate 10 and screws 20 are manufactured from titanium.

Each bone screw 20 includes a head 24 and a threaded shaft 21. Head 24 is formed of three segments 25, each of which has an outside surface 22 that is generally spherical (that is, it is generally as if formed from a segment of a sphere). Each segment 25 is flexibly attached to the shaft 21 and each segment is separated from each of the other segments by a gap 29. It will be noted from the figures and the foregoing discussion that the gap 29 between each segment 25 extends to the threaded shaft 21 and each segment 25 flexes at a periphery of the threaded shaft 21. Each segment 25 includes a generally spherical cap surface 27 and a pin hole 26 defined though cap surface 27, which pin hole is adapted to receive a pin from a driving tool, disclosed below. The segments combine to define an outermost edge 23 of the screw head 24. The overall maximum diameter of head 24 at the outermost edge 23 is capable of being resized as it locks itself into vertebral plate 10 as segments 25 are drawn close to each other by a driving tool, disclosed below. The size reduction allows for a positive snap in by screw 20 within hole 12 as the segments are released by the tool and attempt to return to their original position. The inside surfaces of holes 12 also are spherical to accommodate the overall outside spherical surface of head 24. Other embodiments of screw 20 can include two segments, or more than three segments.

In one embodiment, screw head 24 is made from titanium, and is manufactured by being sectioned into thirds, leaving only a "vertical flexing bar" which is an integral thinned out portion of each segment 25 that connects the spherical portion to shaft 21. The cross-section of the vertical flexing bar portion of segment 25 is controlled to achieve the desired flexure of segment 25 and is manufactured in one embodiment by a lathe or milling machine. The vertical flexing bar should be thin enough so that the driving tool, disclosed below, can flex each segment enough to allow a reduction in the diameter/circumference of the outer surface of head 24 to allow head 24 to fit into hole 12 in a reduced size state. Further, the vertical flexing bar portion of segment 25 should be thick enough so that each segment 25 has sufficient "spring" to retain screw 20 within hole 12 when the driving tool is removed and segments 25 try to expand to normal (i.e., pre-reduced diameter/circumference) size but instead are captured by the inner spherical surface of hole 12 and trapped.

Figure 2:
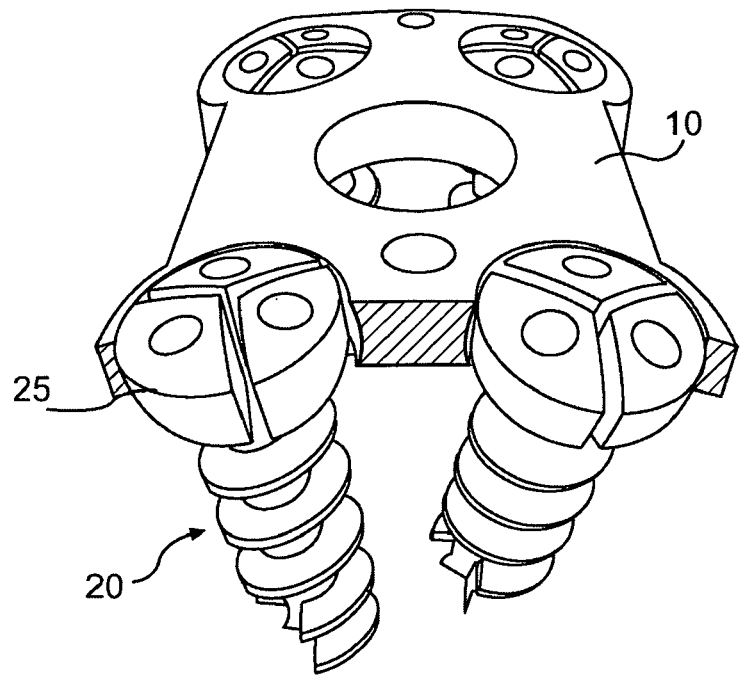
FIG. 2 is a cut-away perspective view of the vertebral plate and bone screws in accordance with one embodiment of the present invention.

FIG. 2 is a cut-away perspective view of vertebral plate 10 and bone screws 20 in accordance with one embodiment of the present invention. FIG. 2 illustrates screws 20 after they have all have been "snapped" into plate 10 because segments 25 have attempted to expand to normal size while inserted into hole 12 and have met the inner surface of hole 12. These screws are now firmly retained in holes 12.

Figure 3:
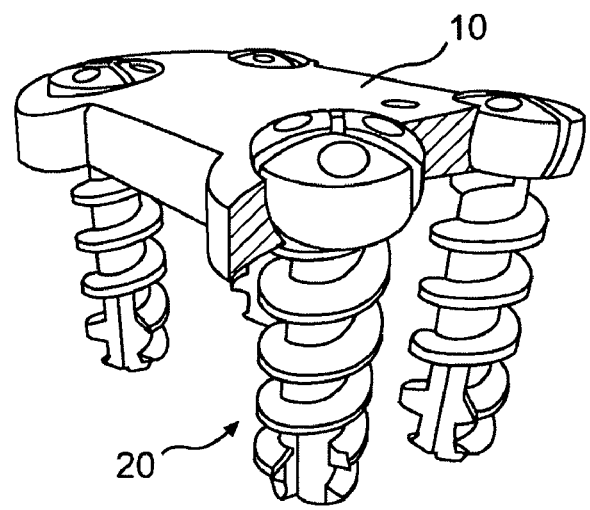
FIG. 3 is another cut-away perspective view of the vertebral plate and bone screws in accordance with one embodiment of the present invention.

FIG. 3 is another cut-away perspective view of vertebral plate 10 and bone screws 20 in accordance with one embodiment of the present invention.

Figure 4:
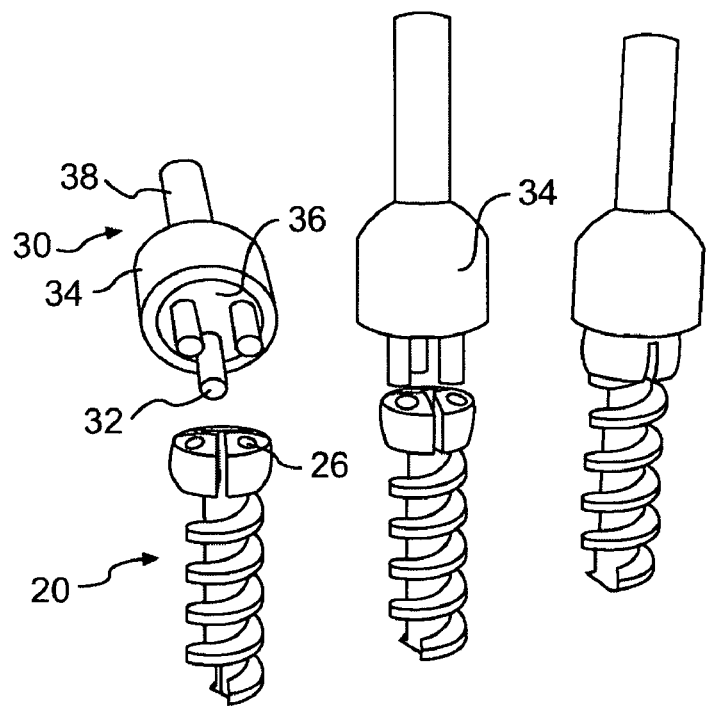
FIG. 4 is multiple perspective views of the screw and a driver in accordance with one embodiment of the present invention.

FIG. 4 is multiple perspective views of screw 20 and a driver 30 in accordance with one embodiment of the present invention. Driver 30 includes a handle 38, a driver head 34, and three drive pins 32. Drive pins 32 are configured to be inserted in pin holes 26 of screw 20. Driver head 34 includes a spherical mating plate 36. The spherical screw head nests itself inside mating plate 36 when inserted with driver 30. Driver 30 reduces the overall circumference of the head of screw 20 as downward pressure is applied to handle 38 because drive pins 32 are drawn together, as disclosed below. Drive pins 32 and inner spherical plate 36 conform exactly to the shape of the screw head in one embodiment, giving it a maximum strength and instilling drive confidence to the user. In one embodiment, driver 30 is manufactured from stainless steel.

Figure 5:
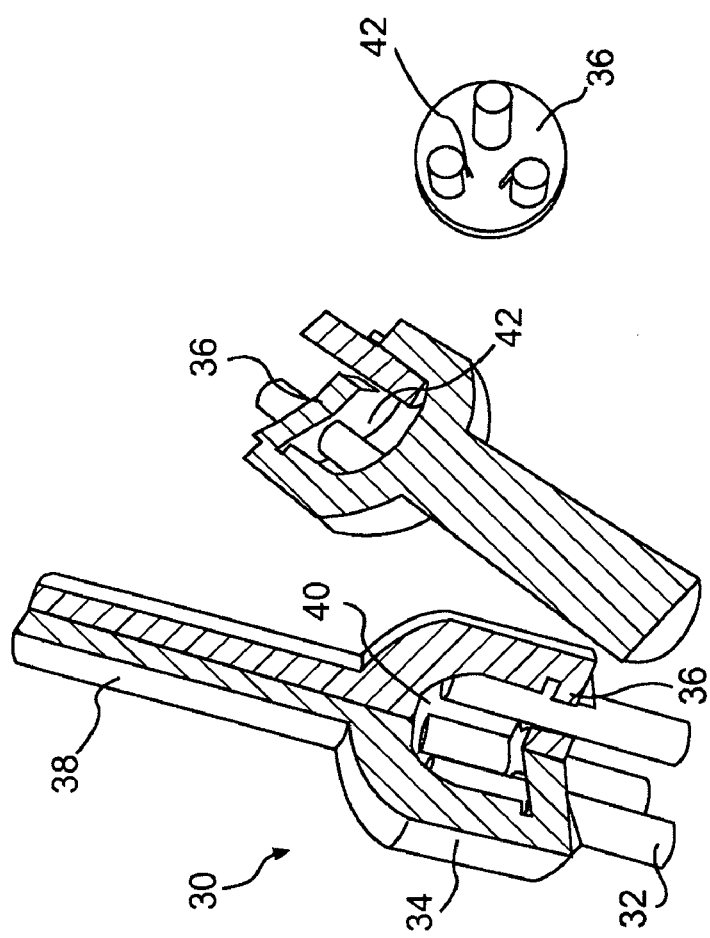
FIG. 5 is a multiple perspective cut-away view of the driver in accordance with one embodiment of the present invention.

FIG. 5 is a multiple perspective cut-away view of driver 30 in accordance with one embodiment of the present invention. Drive pins 32 float in slots 42 of plate 36. Each slot 42 is elongated with its long axis generally along a radius of plate 36 so that pins 32 float along the radius in slots 42. In one embodiment, plate 36 includes O-ring inserts that hold pins 32 within head 34. In one embodiment, plate 36 also is allowed to float within head 34. The view on the right of FIG. 5 is an isolated cut-away view of plate 36 with pins 42.

The inner surface of head 34 includes a tapered surface 40 that causes pins 32 to move towards each other as force is placed on screw 20. Pins 32 are normally in the outer or largest diameter position, and in that position they engage with holes 26 of screw head 24 as shown in FIG. 4. As pins 32 are fully seated in screw 20, additional downward pressure on drive handle 38 causes the tops of all three pins to cone or deflect inward along tapered surface 40. The inward deflection forces the three segments of the screw head inward, reducing its maximum diameter/overall circumference. The combination of rotation of screw 10, and the normal downward pressure of driving screw 10, causes the screw to snap into the plate's spherical cavity, where it is trapped. When the screws are fully tightened, the driver tool can be easily removed, leaving an integral screw and plate system. The finished assembly is a strong, low profile, self aligning screw head system, with a positive lock, and no separate locking pieces required.

The three hardened drive pins 32 that are inserted in holes 26 in screw head 24 drive screw 20. In one embodiment, holes 26 are placed away or outboard from the screw center, where they offer greater torque advantage and minimal or no outward expansion or hoop stresses induced into the shell of the screw head relative to prior art bone screws. The three segment pattern defines a screw head whose outer surface is drawn inward when the screw is installed with the driver, and the inward drawing of the outer surface is maintained by the driver during the tightening operation. This minimizes the chance of cam out or potential fracture due to hoop stresses.

In contrast, known prior art bone screws are driven from a hollow screw center. The center of the screw has the minimum torque arm radius, and will thus have the highest stress level for the screw as well as the driver. Prior art bone screws driven by a hollow center cavity or socket typically have induced outward expansion and the potential of cam out or fracture of the screw due to hoop stresses.

Figure 6:
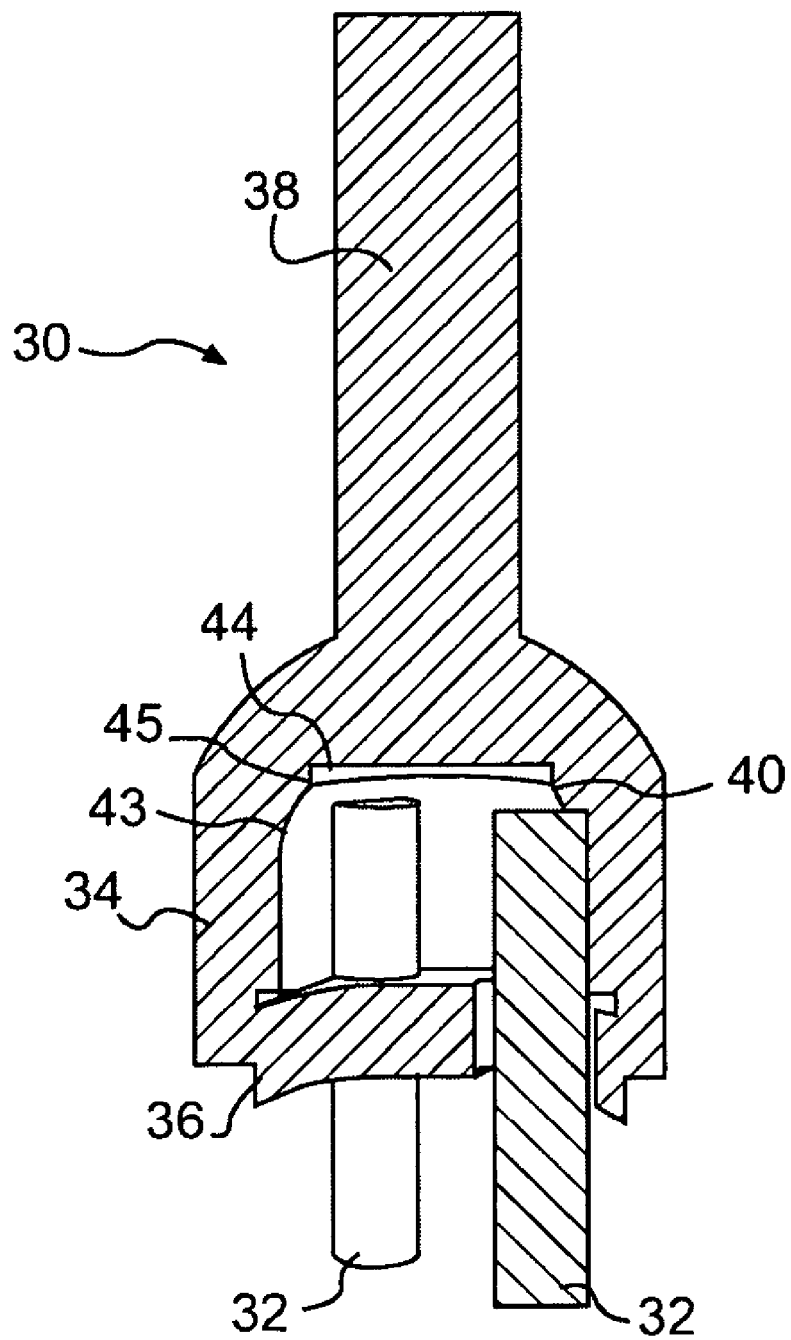
FIG. 6 is a sectional view of the driver in accordance with one embodiment of the present invention.

FIG. 6 is a sectional view of driver 30 in accordance with one embodiment of the present invention. FIG. 6 illustrates how pins 32 interact with tapered surface 40 of head 34. Tapered surface 40 includes a spherical section 43 and a cylindrical section 44 that are joined at a corner 45. As upward pressure is applied to pins 32, the top corner of the pins will be forced inward toward the centerline of driver 30. When the pins reach corner 45, there will be a noticeable snap or click felt at handle 38.

Once the three pins are clicked into cylindrical section 44, they will stay there until they are physically pulled outward/downward. If the bone screw is applied to the pins before this clicking action, and then clicked, the screw will be trapped to the driver, and the screw head will be in its compressed, smallest circumference state. This feature is desirable in that it is applied before the screw is to be inserted through the vertebral plate. The screw will be securely trapped to the driver and already shrunken to the desired diameter for passage through the narrow top opening of the vertebral plate screw hole.

Figure 7:
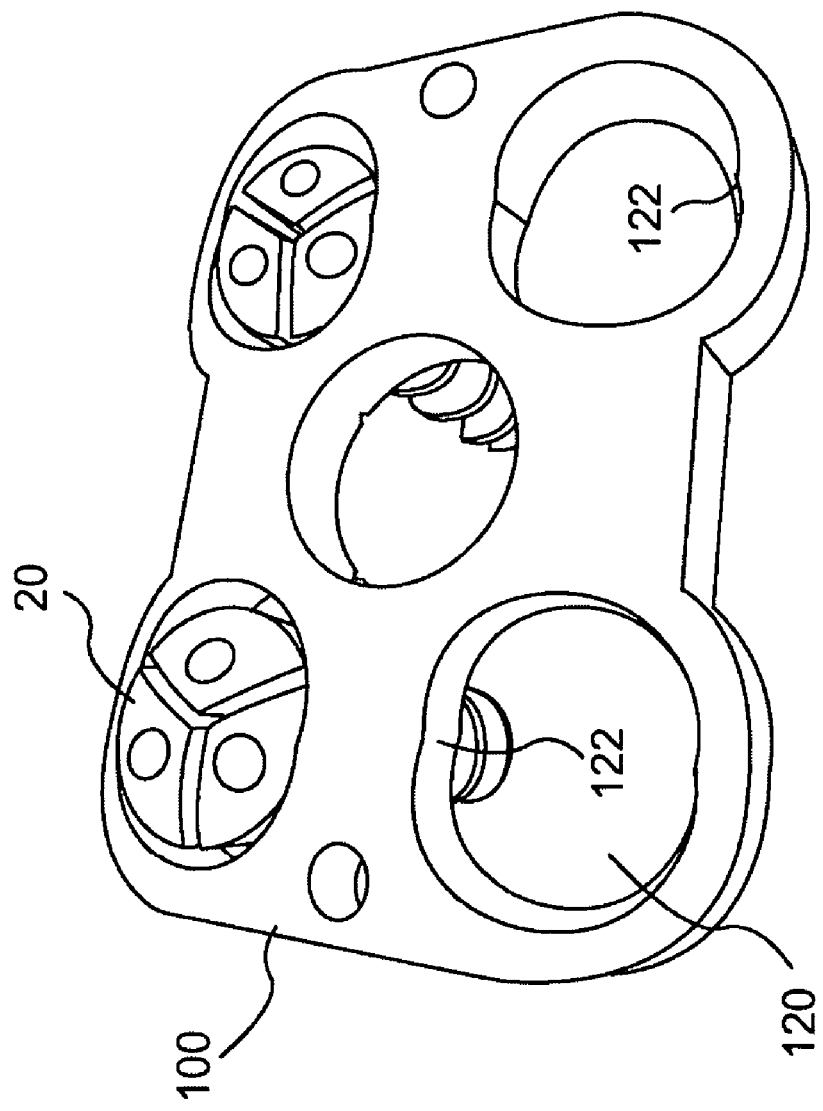
FIG. 7 is a perspective view of a vertebral plate and bone screws that are adapted to be inserted and retained by the vertebral plate in accordance with another embodiment of the present invention.

FIG. 7 is a perspective view of a vertebral plate 100 and bone screws 20 that are adapted to be inserted and retained by the vertebral plate in accordance with another embodiment of the present invention. Plate 100 includes slotted and elongated screw holes 120 having indentations 122. Indentations 122 of holes 120 provide additional retention force on screws 20 by pressing on the outer surface of the screw heads.

Several embodiments of the present invention are specifically illustrated and/or described herein. However, it will be appreciated that modifications and variations of the present invention are covered by the above teachings and within the purview of the appended claims without departing from the spirit and intended scope of the invention.

What is claimed is:

1. A vertebral plating system comprising:
 a bone screw comprising a screw head and a shaft; and
 a driver to install said bone screw, said driver comprising
  an elongated handle,
  a driver head mounted to said handle,
  a generally circular mating plate associated with said driver head and formed with at least one elongated slot angularly displaced about said mating plate, said at least one elongated slot having an elongation axis generally along a radius of said mating plate, said at least one elongated slot having a first end arranged toward a center of said generally circular mating plate and a second end arranged radially outward from said first end; and at least three drive pins associated with said driver head, at least one drive pin of said at least three drive pins being movably supported in said at least one elongated slot and having a first range of motion in an axial direction parallel to said handle and a second range of motion in a radial direction along said elongated slot and generally perpendicular to said first range of motion, movement within said first range of motion resulting in movement within said second range of motion, wherein said screw head has a top surface and an outermost edge defining a circumference of the screw head and comprises at least three head segments each of which is flexibly attached to said shaft, each of said at least three head segments defining in the top surface thereof a pin hole sized and configured to receive one of said at least three drive pins, and wherein said segments are movable, in response to movement of said pins along said second range of motion while within said pin holes, between a relaxed position in which the circumference of the screw head is a first circumference and an inner position in which the circumference of the screw head is smaller than the first circumference, whereby, axial pressure on the handle in the direction of the screw, while the pins are within the pin holes, causes said pins to move in said first range of motion and said second range of motion and reduce the circumference of the screw head, and rotation of the handle with the pins in the pin holes transfers a torque from said driver head to said screw head, to install said bone screw.

2. The vertebral plating system of claim 1, further comprising:
a plate that comprises a plurality of holes, each hole adapted to receive the bone screw.

3. The vertebral plating system of claim 2, wherein each of said segments defines a spherical outside surface.

4. The vertebral plating system of claim 3, wherein said screw head is retained in said hole by outward movement of said segments, when said bone screw head is in said second position.

5. The vertebral plating system of claim 2, wherein each of said holes comprises a spherical inside surface.

6. The vertebral plating system of claim 1, said driver head comprising a tapered internal surface, wherein said drive pins float along said tapered internal surface and translate in a radial direction relative to said mating plate and translate in a longitudinal direction relative to said mating plate.

7. The vertebral plating system of claim 6, wherein said tapered internal surface comprises a spherical surface and a cylindrical surface.

8. The vertebral plating system of claim 1, wherein said mating plate has a spherical contour.

9. The vertebral plating system of claim 8, wherein said screw head has a portion having a spherical contour.

10. The vertebral plating system of claim 9, wherein said portion of said screw head having said spherical contour nests itself inside said spherical contour of said mating plate, when inserted with said driver.

11. The vertebral plating system of claim 9, wherein said spherical contour of said screw head is generally the same as said spherical contour of said mating plate.

12. The vertebral plating system of claim 1, wherein each of said segments is separated from each of the other said segments by a gap.

13. The vertebral plating system of claim 1, further comprising at least one o-ring insert that retains said at least three drive pins within said driver head.

14. The vertebral plating system of claim 1, wherein said mating plate is integral with said driver head.

15. A vertebral plating system comprising:
a bone screw comprising a screw head and a shaft;
a driver to install said bone screw, comprising,
a handle;
a driver head having a tapered internal surface;
a mating plate having at least one elongated slot, said elongated slot having an elongation axis generally along a radius of said mating plate; and
at least three drive pins coupled to said driver head with at least one drive pin of said at least three drive pins floating in said at least one elongated slot, said drive pins contacting said tapered internal surface,
wherein said screw head has an outermost edge and comprises at least three segments each of which is flexibly attached to said shaft, and wherein said segments are capable of inwardly moving to reduce a circumference of the screw head at the outermost edge, wherein said drive pins float along said tapered internal surface and translate in a radial direction and a longitudinal direction relative to said mating plate, and wherein each of said at least three segments comprise a pin hole sized and configured to receive one of said at least three drive pins, and while said drive pins are received within said pin holes, said drive pins act on said screw head to cause said circumference of said screw head to reduce and impart a torque to said screw head to either install or remove said bone screw.

16. The vertebral plating system of claim 15, wherein said tapered internal surface comprises a spherical surface and a cylindrical surface.

17. The vertebral plating system of claim 15, further comprising:
a plate that comprises a plurality of holes, each hole adapted to receive the bone screw.

* * * * *